United States Patent
Day et al.

(10) Patent No.: US 10,964,427 B2
(45) Date of Patent: Mar. 30, 2021

(54) INTEGRATED SYSTEMS AND METHODS FOR EVOLVING STATE PROTOCOLS AND DECISION SUPPORT

(71) Applicant: General Electric Company, Schenectady, NY (US)

(72) Inventors: Andrew Day, Newtown, PA (US); Tamas Fixler, Thornhill (CA); Jeffrey Terry, Lewisville, TX (US); Mohammed Uddin, Kingston (GB); Christopher Donald Johnson, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 258 days.

(21) Appl. No.: 16/147,845

(22) Filed: Sep. 30, 2018

(65) Prior Publication Data
US 2020/0105401 A1    Apr. 2, 2020

(51) Int. Cl.
G16H 40/20   (2018.01)
G16H 10/60   (2018.01)
G06Q 10/06   (2012.01)

(52) U.S. Cl.
CPC .......... *G16H 40/20* (2018.01); *G06Q 10/067* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 8,515,777 B1* | 8/2013 | Rajasenan | G16H 50/30 705/2 |
| 8,585,607 B2* | 11/2013 | Klap | A61B 5/412 600/534 |
| 10,483,003 B1* | 11/2019 | McNair | G16H 10/60 |
| 2007/0185739 A1* | 8/2007 | Ober | G16H 40/20 705/3 |
| 2010/0198755 A1* | 8/2010 | Soll | G06F 19/3481 706/11 |
| 2011/0125539 A1* | 5/2011 | Bollapragada | G06Q 10/043 705/7.12 |
| 2012/0296675 A1* | 11/2012 | Silverman | A61B 5/7275 705/3 |
| 2013/0304499 A1* | 11/2013 | Rangadass | G16H 40/63 705/2 |
| 2014/0195258 A1* | 7/2014 | Burton | G06Q 10/0633 705/2 |
| 2014/0236630 A1* | 8/2014 | Murata | G06Q 50/22 705/3 |

(Continued)

*Primary Examiner* — Michael Tomaszewski
*Assistant Examiner* — Jay M. Patel

(57) ABSTRACT

Methods, apparatus, systems and articles of manufacture are disclosed to manage care pathways and associated resources. An example apparatus includes a system monitor to coordinate a patient data analyzer and a care pathway processor to at least: identify a first patient record associated with a first care pathway; and identify a second patient record that is not on the first care pathway but should be on the first care pathway. The example apparatus includes a graphical user interface including information regarding, in a first area, the first patient record associated with the first care pathway and, in a second area, the second patient record that should be associated with the first care pathway.

20 Claims, 10 Drawing Sheets

(56) References Cited

U.S. PATENT DOCUMENTS

| | | | | |
|---|---|---|---|---|
| 2014/0303670 A1* | 10/2014 | Colloca | .................. | A61B 17/66 |
| | | | | 606/237 |
| 2015/0019259 A1* | 1/2015 | Qureshi | .............. | G06F 19/3481 |
| | | | | 705/3 |
| 2015/0066524 A1* | 3/2015 | Fairbrothers | .......... | G16H 50/20 |
| | | | | 705/2 |
| 2015/0213223 A1* | 7/2015 | Amarasingham | ...... | G16H 50/30 |
| | | | | 705/2 |
| 2015/0370967 A1* | 12/2015 | Powell | .................. | G16H 50/20 |
| | | | | 705/2 |
| 2016/0042135 A1* | 2/2016 | Hogan | ................... | G16H 50/20 |
| | | | | 705/2 |
| 2016/0198996 A1* | 7/2016 | Dullen | ................ | A61B 5/02055 |
| | | | | 600/301 |
| 2016/0354039 A1* | 12/2016 | Soto | ........................ | G06Q 40/08 |
| 2016/0371441 A1* | 12/2016 | Day | ........................ | G16H 40/20 |
| 2017/0351820 A1* | 12/2017 | Van Halteren | .......... | G06N 5/022 |
| 2018/0060521 A1* | 3/2018 | Connolly | ............. | G06F 19/3418 |
| 2018/0132756 A1* | 5/2018 | Kording | ................ | G16H 40/67 |
| 2019/0042838 A1* | 2/2019 | Bose | .................... | H04N 17/002 |
| 2019/0206570 A1* | 7/2019 | Colister | ................ | G06F 3/0482 |

\* cited by examiner

FIG. 5

SEPSIS CARE

SEPSIS FLAG-NO TREATMENT  4/72

| Time from detection | Patient | Status flags | Unit bed |
|---|---|---|---|
| 3h 50m | A.Jar JHH0231342 | Confirmed | MED NLS04-443 |
| 2h 20m | H.Bur JHH3453222 | At risk | SURG MBG3-005 |
| 6h 15m | B.Pin JHH3455647 | Negative | MED NLS04-335 |
| 1h 15m | R.Sul JHH3455444 | Negative | MED MEY9-004 |

BUNDLE  2/30

| Elapsed time | Patient | Orders | Unit bed |
|---|---|---|---|
| 3-Hour resuscitation | | | 1 |
| 2h 20m Neuro | S.Ren JHH2342341 | Antibiotics | MED MEY8-223 |
| 6-Hour septic shock | | | 1 |
| 2h 20m ICU | K.Jih JHH56745232 | Lactate level  Vasopressors | MED MPCU-008 |

SOURCE CONTROL  1/10

| Patient | Infection procedure |
|---|---|
| T.Hir JHH2234234 | Abscess Ordered surgery +3h |

Elevated  1/15

| Patient | Status flags | Unit bed |
|---|---|---|
| M.Hal JHH67599 | At risk | MED MEY8-004 |

Other sepsis  2 of 25

| Patient | | Unit bed |
|---|---|---|
| J.Kin JHH67599 | | GYN WGB4-407 |
| F.Log JHH69899 | | GYN WGB4-415 |

Peds  2 of 8

| Patient | | Unit bed |
|---|---|---|
| A.Lee JHH67511 | | PED ZB09N-030 |
| M.Joh JHH67329 | | PED ZB09S-032 |

Total sepsis load  110

| Confirmed | At risk | Elevate | Bundle | Other sepsis | Peds |
|---|---|---|---|---|---|
| 32 | 25 | 15 | 3 Hour 12  6 Hour 18  30 | 25 | 8 |

INTEGRATED SYSTEMS AND METHODS FOR EVOLVING STATE PROTOCOLS AND DECISION SUPPORT

FIELD OF THE DISCLOSURE

This disclosure relates generally to care protocol management, and, more particularly, to integrated systems and methods for evolving state protocols and decision support to dynamically schedule healthcare operations over a current and future time horizon for a plurality of patients.

BACKGROUND

Patient care can be organized according to one or more care pathways including milestones, tasks, resources, and personnel to care for the patient. Certain care pathways are known, along with associated clinical metrics which indicate a patient's health state. Such clinical metrics can be monitored by care providers to help ensure they are stable. When stable, the care providers are able to handle a clinical workflow and a hospital's physical resources have capacity. However, when care pathways are uncertain, the care providers may not have capacity to serve at any instant and the states of the patients being cared for may be either unstable or evolving in a way that is not readily detected.

Ongoing and evolving care delivery protocols vary in response to changes in managed clinical measures over time, and their clinical effects are influenced by the accumulated interactions of a patient with the hospital's physical environment as well as dissociated routine actions of a plurality of care providers, staff, and visitors. Such protocols are difficult to optimally manage. These protocols are not well bounded by a singular event or alarm level. Their incremental change effects may be difficult to measure. Further, existing physical and care delivery protocols are underdeveloped to sense, design and deliver in response to change, given that their delivery occurs via a plurality of providers and that the underlying clinical state evolves or changes over time. As a result, clinical degradation can occur, and a response to intervene and prevent the degradation is too slow to have an effect. Further complicating this class of care are compound detection and conditional diagnostic steps which yield interim probabilities as to the specific care pathway and protocols that should be executed in the current time and/or planned for future.

BRIEF DESCRIPTION OF THE DRAWINGS

FIGS. 5-6 illustrate example graphical user interfaces monitoring care pathways and compliance and classifying patients into a plurality of care pathway designations with prescribed clinical tasks to drive a system control that orchestrates care delivery.

The figures are not scale. Wherever possible, the same reference numbers will be used throughout the drawings and accompanying written description to refer to the same or like parts.

BRIEF DESCRIPTION

Figure 1:
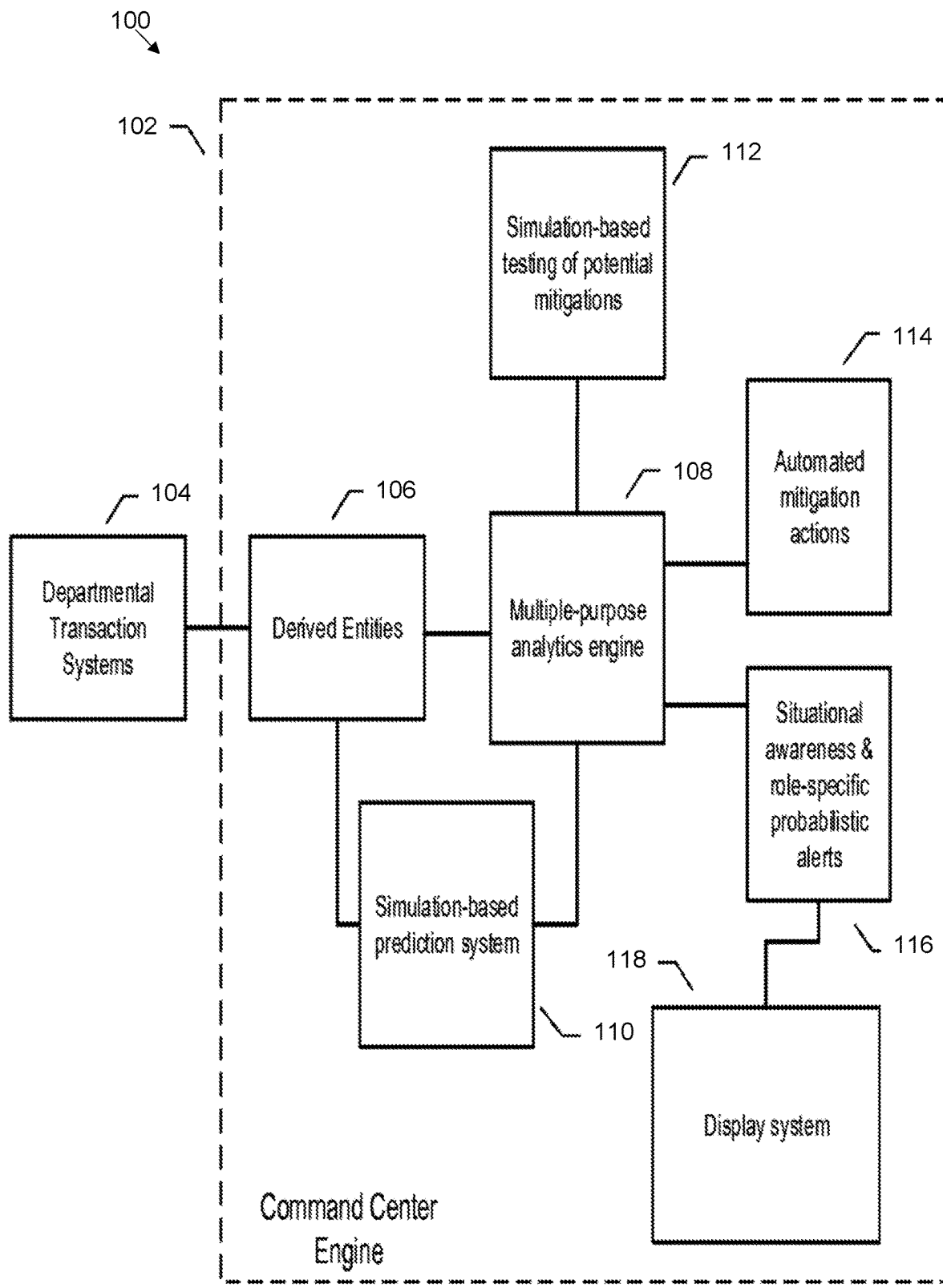
FIG. 1 depicts an example control system for a healthcare facility.

Certain examples provide care protocol management through integrated systems and methods for evolving state protocols and decision support.

Certain examples provide a care pathway management apparatus including a patient data analyzer to compute a clinical response time for one or more patients of the healthcare facility. The example apparatus includes a care pathway processor to model tasks for one or more protocols associated with a care pathway for one or more patients in a cohort grouping and an associated time to execute the modeled tasks, the care pathway processor to prescribe a task for a resource in a current time to reduce at least one of a future adverse clinical condition or a future excess response time for one or more patients. The example apparatus includes a system monitor to coordinate the patient data analyzer and the care pathway processor to at least: identify a first patient record associated with a first care pathway; and identify a second patient record that is not on the first care pathway but should be on the first care pathway. The example apparatus includes a display driver to generate and display a graphical user interface including information regarding the first patient record associated with the first care pathway and the second patient record that should be associated with the first care pathway, the display driver to display the first patient and associated care pathway information in a first area of the graphical user interface and to display the second patient in a second area of the graphical user interface. The example apparatus includes an interaction engine to facilitate interaction, via the graphical user interface, with the first patient record and the second patient record.

Certain examples provide a non-transitory computer readable storage medium including instructions which, when executed, cause at least one processor to at least: process patient data for a healthcare facility to compute a clinical response time for one or more patients of the healthcare facility; prescribe a task for a resource in a current time to reduce at least one of a future adverse clinical condition or a future excess response time for one or more patients, the task selected from a group of modeled tasks for one or more protocols associated with a first care pathway for one or more patients in a cohort grouping and an associated time to execute the modeled tasks; identify a first patient record associated with a first care pathway; identify a second patient record that is not on the first care pathway but should be on the first care pathway; generate and display a graphical user interface including information regarding the first patient record associated with the first care pathway and the second patient record that should be associated with the first care pathway, the graphical user interface to display the first patient and associated care pathway information in a first area of the graphical user interface and to display the second patient in a second area of the graphical user interface; and facilitate interaction, via the graphical user interface, with the first patient record and the second patient record.

Certain examples provide a computer-implemented method including processing, by executing an instruction using at least one processor, patient data for a healthcare facility to compute a clinical response time for one or more patients of the healthcare facility. The example method includes prescribing, by executing an instruction using at least one processor, a task for a resource in a current time to reduce at least one of a future adverse clinical condition or a future excess response time for one or more patients, the task selected from a group of modeled tasks for one or more protocols associated with a first care pathway for one or more patients in a cohort grouping and an associated time to execute the modeled tasks. The example method includes identifying, by executing an instruction using the at least one processor, a first patient record associated with a first care pathway. The example method includes identifying, by executing an instruction using the at least one processor, a second patient record that is not on the first care pathway but should be on the first care pathway. The example method includes generating and displaying, by executing an instruction using the at least one processor, a graphical user interface including information regarding the first patient record associated with the first care pathway and the second patient record that should be associated with the first care pathway, the graphical user interface to display the first patient and associated care pathway information in a first area of the graphical user interface and to display the second patient in a second area of the graphical user interface. The example method includes facilitating interaction, via the graphical user interface by executing an instruction using the at least one processor, with the first patient record and the second patient record.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

Certain aspects of the present disclosure describe methods, systems, apparatus, and non-transitory computer readable media for automated workflow management and associated resource configuration. For example, a subject in a recuperating state is monitored using one or more sensors to acquire one or more physiological parameters. Clinician judgement may also be entered in direct parametric or a derived form. Further, a clinical trajectory of the subject at a specific time is detected using the physiological parameters and a judgement of care providers as entered into a care protocol delivery system.

Certain examples manage stable and unstable profiles of care. In unstable care pathway situations, which occur in complex cases such as, sepsis, delirium, and other conditions that can have non-linear diagnosis and degradations in health state and whose clinical response in an emergency can overwhelm care providers who are providing service to a plurality of patients. An individual patient and an associated cohort consume shared clinical resources and can be dynamically managed. Each patient and relevant cohort(s) are bound by assigned attributes such as diagnosis, care pathway, urgency, rate of change of clinical state, medication(s), hospital and care provider resource requirements, etc. The patient and related cohort(s) can be evaluated to determine an associated/appropriate care pathway and compliance with that care pathway, for example.

Certain examples manage, track, and otherwise enable care pathways with evolutionary patient state, a plurality of clinical measures and prescriptive intervention so as to avoid what will otherwise become a clinical demand that cannot be served. Certain examples provide new systems and methods to manage such evolving care pathways to help ensure more stable patients.

Certain examples provide an integrated system to enable the achievement of care delivery for protocols in complex environments, such as hospitals, in which one or more clinical measures are evolving through time so that the care delivery process that diagnoses and manages patient states may respond in a shorter time constant than a time during which one or more underlying clinical metrics change, and may be assigned by an automated care delivery system to be delivered with sufficiently advanced time to avoid an unscheduled clinical intervention driven by an emergency or alarm. Examples of care delivery protocols enabled by the disclosed system include sepsis and delirium.

In certain examples, compliance with a given care pathway is determined by a combination of a clinical diagnosis to determine a medical condition and monitoring of the patient with one or more sensing systems to compare biometrics with desired levels. Additionally, certain diagnostics and/or care protocol actions are prescribed, and those prescribed actions may or may not be followed. Example systems and methods to monitor and help ensure protocol adherence are provided by Johnson, et al., in U.S. Pat. No. 9,785,744, which is incorporated by reference herein.

Certain examples track care providers and patients and progress on a care pathway to translate clinical metrics into care delivery tasks that may be executed by care providers and/or patients. Certain examples provide an improved technological infrastructure to better manage care pathways to help prevent care providers from becoming overwhelmed, which results in damage to patient, and provider, health and safety. Avoiding unscheduled clinical workflow is achieved by anticipating where a clinical metric will be at a future time and intervening within the time constant to prevent occurrence of condition(s) that otherwise (without the disclosed systems and methods) could lead to breakdowns in system workflow tasks, for example. Exceptions with respect to available staff and equipment, predicted clinical state versus desired clinical measures, and missing execution of tasks in one or more locations or functions of the clinical enterprise in a care delivery protocol each can categorize a patient and/or healthcare facility as being in an exception status and/or otherwise in noncompliance with tasks from pathway-specific order sets, etc. Exceptions can occur in real-time and/or at a projected future time, for example.

Sensors and systems in a hospital and/or other healthcare facility's operational control environment provide data input to drive determination/prediction which can be used to adjust resources for care pathway compliance.

Systems can be affected by a determination that a patient is out of compliance or is likely to soon be out of compliance with his/her chosen care pathway. For example, an associated order set and affected systems can be reprogrammed, reserved, triggered, etc., to account for the exception/deviation from the care pathway.

FIG. 1 depicts an example control system 100 for a healthcare facility. The example system 100 can provide probabilistic cross-system forecasting, alerting, improvement/optimization, etc. The example system 100 includes a command center engine 102, which facilitates the collaboration of cross functional teams using data from department-wide systems to manage the hospital operations. Certain examples include functions such as admitting, bed management, scheduling, staffing, environmental systems, transport dispatchers and other related functions, for example.

In certain examples, the command center engine 102 can parse data from multiple departmental transactional systems 104. For example, a real-time HL7 message broker can provide patient-related information to the command center engine 102, and an enterprise service bus can provide system data to the command center engine 102. Data received from these systems is parsed, transformed and integrated into by the command center engine 102 into derived entity structures 106 (e.g., stored in one or more data injection servers, etc.). In certain examples, the derived entities 106 and raw system data persist in one or more database servers. These derived entities 106 are queried by a multiple-purpose analytics engine 108 and also provide input to a simulation-based prediction system 110. The simulation-based prediction system 110 provides probabilistic forecasts to the multiple-purpose analytics engine 108. The near real-time and forecasted information is used by the multiple-purpose analytics engine 108 to generate information about the operational state of the healthcare environment, its patients, its protocols, its staff, and/or other operations, for example. The multiple-purpose engine 108 provides automated mitigation actions 114 to other healthcare facility systems and personnel and also provides situational awareness and role-specific probabilistic warning and alert states 116. In certain examples, information is provided to users in the command center engine 102 and elsewhere in the healthcare system in the form of analytic tiles. Probabilistic alert information is used to take distinctive actions, based on rules, to mitigate defects and constraints automatically detected by the system, for example.

Certain examples provide predictive mechanisms 110, 112 that are simulation based, using discrete event and agent based methods singularly and in combination to execute the prescribed and conditional clinical tasks with resources and evolving state patient models in the time domain, which can be the current and future interval. Other modeling methods such as regression and Bayesian based are optionally utilized.

As an example, the command center engine 102 can use cross-system data, forecasts and probabilistic alerts to automatically and optimally control patient discharge and environmental services activity to better serve patients and improve hospital operational performance, such as reducing waiting delays for procedures and accelerating discharges. Data is extracted from multiple disparate systems 104, including perioperative/procedural, diagnostic imaging (DI), labs, therapy, transfer center, emergency department (ED), bed management, and/or admitting, etc. After being parsed, transformed, and integrated into derived entities 106, calculations are performed by the multiple-purpose analytics engine 108 and the simulation-based hospital operations prediction system 110 to identify states that indicate how patient flow is currently occurring or will occur in the forecasted future, current and/or forecasted/projected patient care pathway compliance, etc. A defect state can be determined based on one or more criterion/threshold such as a threshold time interval, a treatment protocol (e.g., a diet protocol, an exercise protocol, a spirometry protocol, a rest protocol, etc.), a position/location, other care pathway element, etc. These defect states are calculated in real-time (or substantially real-time given data retrieval, transmission, and processing latency(-ies)) and are also projected over a forecast interval such as the next 48 hours, etc., using inferences, probabilistic calculations and the results of the simulation-based hospital operations prediction system 110. In certain examples, defect states that are determined to be urgent are set with a configurable threshold and trigger follow-up events to investigate and/or remedy the defect state. The dynamic alerting and clinical resource scheduling may be activated for "current time" and/or in anticipation of a computed future time, for example. The defect states and suggested mitigation can be communicated via several methods including on a "priority discharge tile" via a display system 118 in the command center engine 102, for example.

Figure 2:
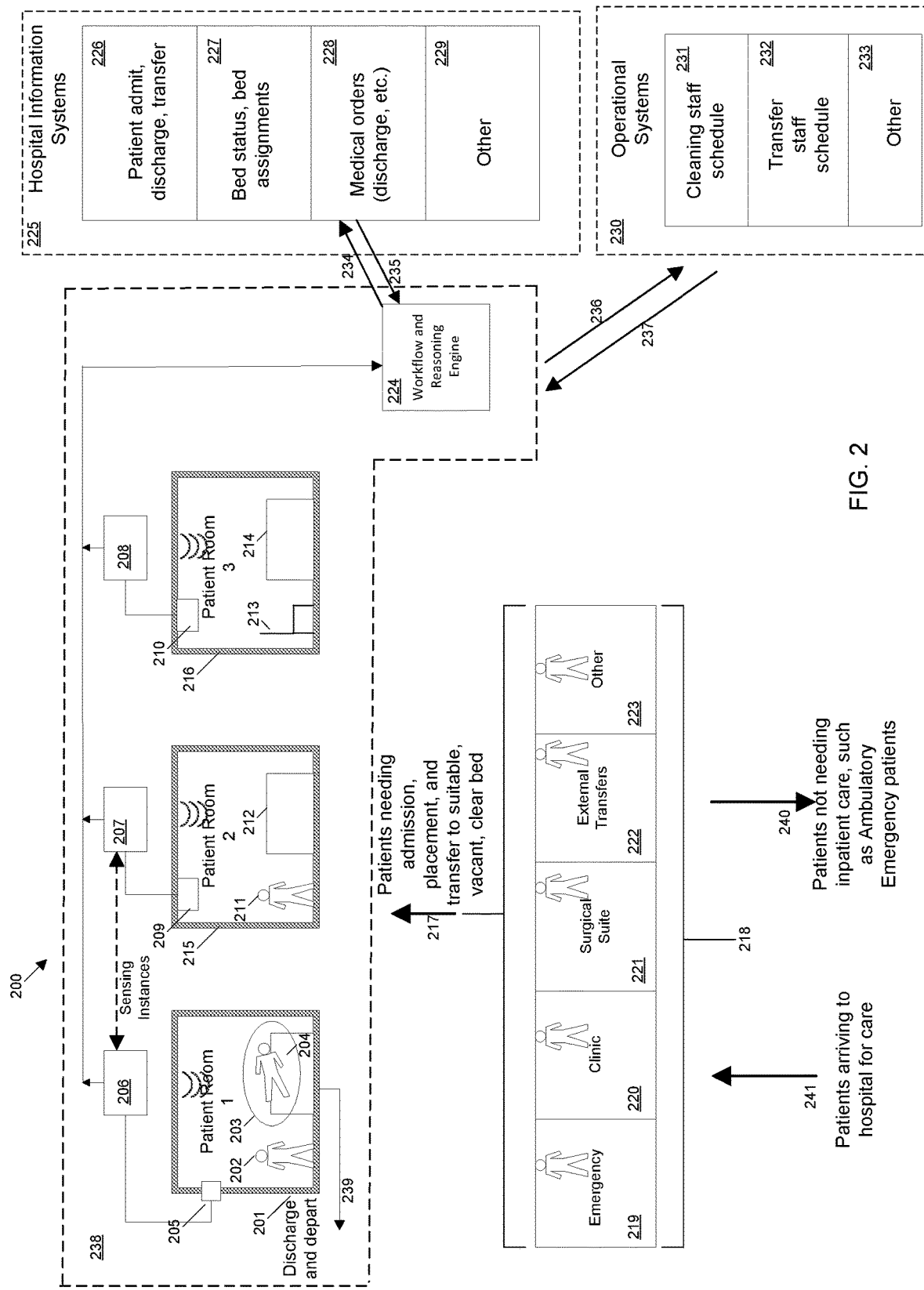
FIG. 2 illustrates a schematic of an example monitoring network in the context of a healthcare facility environment.

FIG. 2 illustrates a schematic of an example monitoring network 238 in the context of a healthcare facility environment 200 (e.g., a hospital, clinic, doctor's office, surgical center, etc.). The example monitoring network 238 communicates with the command center engine 102 to provide the command center engine 102 with operational data regarding the healthcare facility environment 200, which includes care providers, physical space, equipment, consumables and etc. As shown in the example of FIG. 2, a workflow engine 224 and a plurality of sensing components 206-208 (e.g., Doppler sensor, optical sensor, clinical devices, etc.) are installed in patient rooms 201, 215, 216. Each room 201, 215, 216 includes one or more people 202, 203, 211 (e.g., patients, physicians, other personnel, etc.), furniture 204, 212, 213, 214 (e.g., patient bed, chair, examination table, etc.), and electronics 205, 209, 210 (e.g., medical equipment, lighting, fan, camera, detector, etc.). The sensing components 206-208 gather data based on biometric measures, objects, movement, and/or other state/status information in the rooms 201, 215, 216, for example.

The workflow engine 224 is also linked to a hospital information system 225 which may include multiple data systems 226-229 (e.g., a patient admit discharge transfer (ADT) system, a bed status/assignment system, a medical order system, etc.). The workflow engine 224 is also connected to existing hospital operations management systems 230 (also referred to as hospital operational systems or operational systems, for example) which may include various resource location, scheduling and staff (resource) control systems 231-233, for example.

The workflow engine 224 can manage the timely transition of patients throughout the hospital system 200 in both the current time and simulated future time. Patients requiring care 241 may arrive at the hospital via a number of circumstances 219-223 including through the Emergency room 219, from surgery in an operating room 221 or other methods (e.g., clinic 220, external transfer 222, other 223). Although some arrivals may be able to later depart 240 without an inpatient stay, many patients 217 will require further care in an inpatient bed 204.

In many hospitals, inpatient bed capacity is highly utilized, resulting in a scarcity of suitable inpatient beds 204, 212, 214 available for new admissions which then slows and restricts the process of admission 217. Inpatient bed capacity is released when a current patient 203, 211 occupying the bed 204, 212 is discharged 239 from the hospital. However, before a new admission can occupy this bed 204, 212, the previous discharge must be made known to hospital staff and recorded in hospital information systems 226, 227. Then the bed and room must be cleaned and the new patient transported to the room. This discharge and cleanup process is frequently delayed due to a lack of awareness of the specific timing of the departure of a discharging patient as well as delays or gaps in time arising due to manual activation of operational activities, for example.

Using the sensing components 206, 207, 208 and the workflow engine 224, certain examples improve and streamline a patient's care path at the healthcare facility and can track their location and progress and automate activation and guidance of appropriate operational activities to help keep a patient on his/her care pathway, bring the patient back in compliance with his/her care pathway, start a patient along a care pathway, trigger an alert for non-compliance, etc. Automated detection of departure with automated activation and guidance of appropriate operational activity can help to reduce instances of wide departure from care pathway tasks, milestones, etc.

An example of the system's operation includes evaluating hospital data to identify a specific patient in a room. For the identified patient, the example system 200 confirms the patient's care pathway and monitors the patient's progress through actions in the care pathway for the particular location, particular time, etc. Thus, the system 200 can monitor the patient in a room to help ensure that the patient has completed a spirometry protocol for a certain prescribed time period in the appropriate location with spirometer, monitor, etc., for example. Similarly, for clinical workflows such as those relating to evolving care, diagnostics steps and/or other actions may be managed, such as attaining a patient's body temperature and then, conditionally, securing a white blood cell count in a sepsis pathway. The example system 200 monitors the patient and can trigger additional actions if the patient is compliant, non-compliant (e.g., if care pathways are occurring or not), etc.

As an example of activity monitoring, various instances of the occupancy sensing component 206-208 can be installed in patient rooms 201. These components 206-208 may be positioned above ceiling tiles or in other fashions that do not compromise patient privacy and may be able to harvest power from existing lighting 209 or other components 205, 210. The sensing components 206-208 can be activated by the workflow engine 224 to monitor specific rooms to determine whether they are currently in active use. Based on a combination of sensing results and hospital information system data, the workflow engine 224 can determine whether to activate specific hospital operational functions, for example. It can be appreciated that other sensing systems are incorporated such as clinical devices.

Figure 3A:
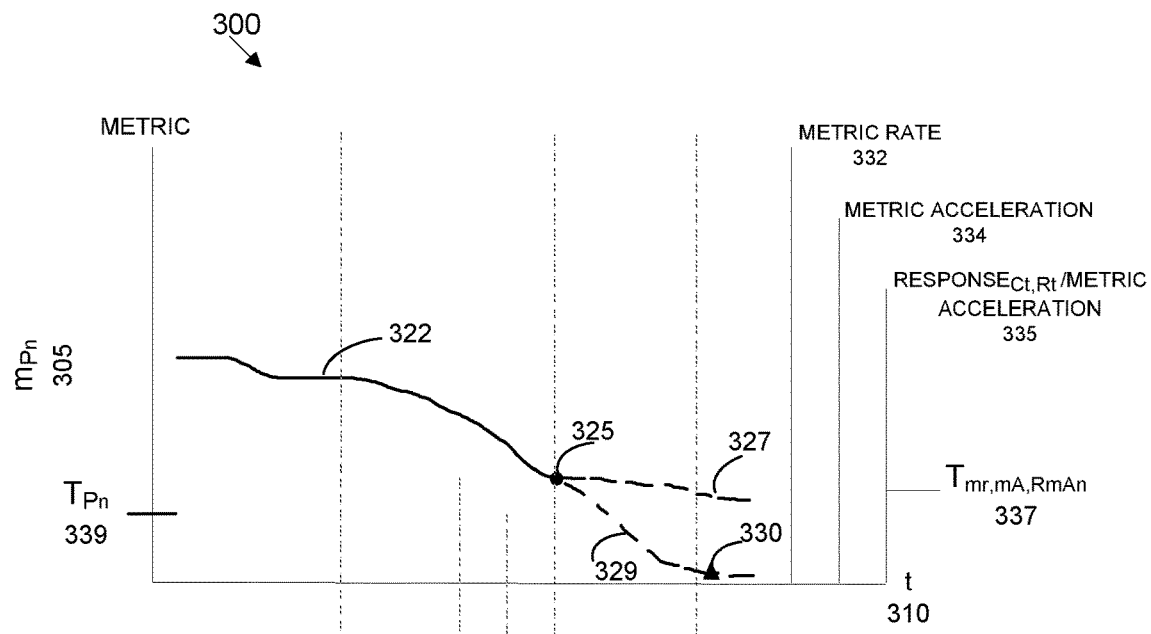
FIGS. 3A-3B illustrate a schema driving adherence to one or more clinical metrics for a patient following a care pathway and associated protocols over time.
Figure 3B:
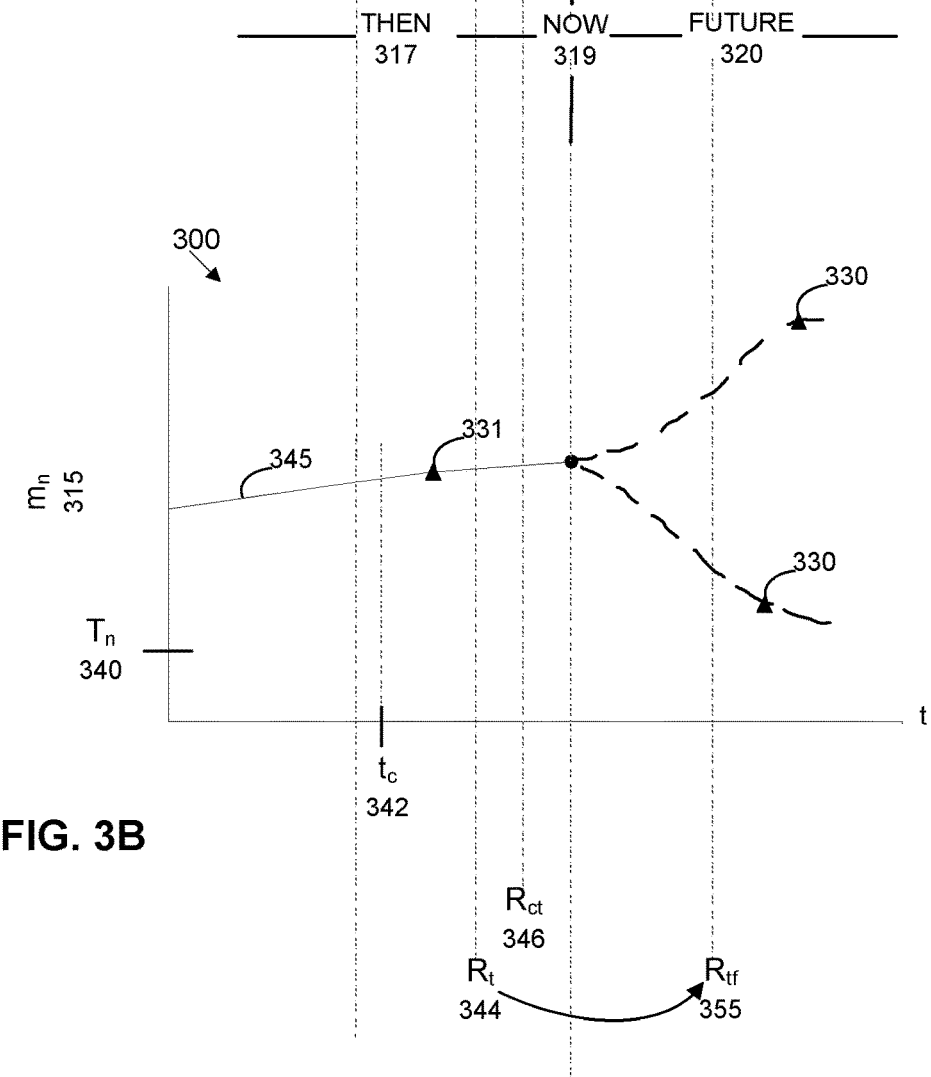

FIGS. 3A-3B illustrate a schema 300 driving adherence to one or more clinical metrics for a patient following a care pathway and associated protocols over time. The example schema 300 of FIG. 3 reflects a method of optimally managing care delivery protocols. As demonstrated by the example schema 300, evolving care protocol automation triggers clinical workflows driven by the command center engine 102 and/or the workflow and reasoning engine 224 ahead of a degraded clinical condition.

The example of FIG. 3A provides an outline of evolving care protocol automation for treatment of sepsis. Other conditions such as delirium, etc., can be similarly monitored, automated, and improved or corrected. The example time series representation 300 of FIG. 3A shows a change in a clinical metric 305 being monitored over time (t) 310. The metric 305 ($mp_n$) is the primary metric being controlled for a patient n to achieve a desired clinical outcome at a point in time. The system 100 controls for one or a plurality of patients and one or a plurality of outcomes per patient. The clinical metric 305 is captured in time series form from one or more sensing devices.

The clinical metric ($m_n$) 315, shown in the example of FIG. 3B, is the plurality of metrics n for which the example care delivery process is controlled, in addition to a primary metric 305. In certain examples, there may be one or more clinical indicators that are to be controlled, and there may be one or more care providers or functions in the care protocol that the system is managing. In contrast to the time series for clinical metric 305, the metric 315 is focused on the care provider and/or protocol response dynamics in the factors prescribed by the care pathway being managed.

As shown in the example of FIG. 3A, time 310 is a measure of time domain in seconds, minutes, hours, etc. A time increment for clinical control can be set by a clinician and/or automatically by the system, in which case the underlying time series data acquired with the system is averaged and/or is assigned a probability for the duration of the time increment. As an example, for a sepsis protocol, on average, a 48 hour look back 317 and a 24 hour future 320 are used; however, the system, as a function of clinical diagnostics and rate or acceleration of change of the primary or secondary metrics, may focus the time domain to the last 4 hours and 2 hours of predicted future. The accumulated interval is also adjustable by the user and/or automated method. An interval time constant 342 may be the patient's length of stay as of a certain time or represent a rolling window of time series data, which can include a historical data set and a future time for predicted metrics, for example. As depicted in the example of FIG. 3A, the time interval 310 captures a transient of one clinical measure for a given patient, and the increment of time is not designated in the example of FIG. 3A.

As an example of time increment with respect to the transient, if the metric 322 has changed from an acceptable level to a current level 325 (e.g., a trigger level, $T_{P_n}$, 339, etc.), then the rate of change and/or the acceleration of the metric's change can be used to set the duration of computed data points in the time series and set the automatically scaled display so that the historical transient 317, predicted 320 trajectories 327, 329, and predicted response time trigger of clinical care providers 337 are computable at an error rate sufficiently low with respect to the data sample rate of the raw clinical data, such that clinical care delivery action 330 is differentiatable with respect to the clinical care delivery decision, decision points 344, 346, 355, and/or automated recommendation or implementation of the protocol being managed, for example. The predicted response time, $T_{mr,mA,RMAn}$, 337 is a trigger point or threshold based on a change in rate (mr), a change in acceleration (mA), and/or a change in response (RMAn), for example.

The time domain is divided into the past 317, the current 319, and the future 320. The past 317 represents a historical level of the controlled metrics for one or more patients. The current or present 319 represents current metric(s) for one or more patients. The future 320 represents a time in the future for which the delivery of care is being controlled at which the one or more clinical indicators or metrics for one or more patients are to have been achieved.

A representative of metric value 322 is a time series of the metric 305 for the corresponding patient from a prior time 317 until the current time 319. At the current time 319, the particular metric 322 may unfold and be realized across any number of future predicted trajectories such as an upper bound 327 and a lower bound 329. The indication 322, 325 of the metric 305 over time 310 may have a level, value, or other threshold at which the care delivery protocol should be changed or the settings of an existing protocol should be adjusted to avoid a clinical indicator that would be more adverse at a future point of time. For example, as shown in FIG. 3A, the metric value 322 for a given patient is trending to a level 330 that is a precursor of an adverse clinical indicator that the patient should not experience. Based on the prediction of the value 330, rules can be triggered to limit the further degradation of the subject metric 305. While the example 300 of FIG. 3A shows the value 330 as a low numerical value of the targeted metric 305, it can be appreciated that a high metric level may also be a detriment to the patient and similarly trigger a clinical intervention with sufficient lead time to avoid the indicator proceeding to an undesirable level. The threshold value 330 in the example of FIG. 3A represents a high or low metric or clinical indicator for one or more indicators on one or more patients, for example. The clinical action may also be, for example, a test or other clinical event to improve diagnosis or forecast confidence of the clinical state and/or the response rate of the care providers.

In certain examples, a rate of change in the value 322 of the metric 305 determines an urgency of intervention by the care delivery system (e.g., a combination of care protocols, equipment, tests, people and medication). A metric rate 332 represents a rate of change of the metric(s) 305, 322 and the derivation of points in time at which a historical change in metric(s) will result in an adverse clinical indication that exists at a future 320 point in time given no intervention. If a predicted response rate 332 of the metric 305 for a given patient, taken in combination with its path 322, degrades to a trigger point or threshold value, $T_{Pn}$, 339, a corrective intervention, to have a beneficial effect, is to be assigned by the care protocol system before the metric(s) 322 have a computed probability of reaching an undesirable state. Conversely, an intervention that is positively beneficial may be assigned by the system to decrease the time for beneficial outcomes and/or may be administered to reduce the probability of overshooting a control point for the targeted metric(s) 305. The intervention being automatically assigned is triggered, Tn, 340 at a preceding time. For example, the trigger 340 occurs prior to an observed/tested response time 344 so that the predicted future level 330 of the metric 305 is within a range of values 327, 329 specified by the protocol.

The system 102 also computes a derivative 335 of the metric change rate 332 where the metric(s), for example, may obey an archetype pattern, such as determining that a value of metric Y 305 at a future time 319=a value of the metric 322+a rate of metric change (t) 332+½ acceleration $(t)^2$ of metric change 334, for example. Other examples include applying machine learning regressions, multivariate statistics using time, metric level, rate of metric change, acceleration of metric change and other causal factors as may be determined and monitored, etc., to determine a rate of change, future metric value, etc.

The system 102 also computes a relationship between the observed clinical response time 344 and the computed response time 346 (shown in FIG. 3B), divided by the metric's 305 change acceleration 334 over a "what-if" interval or a time constant 342. The response time is the aggregated duration of detection, diagnosis, personnel response, intervention duration and biological response. The inclusion of these and other activities or responses is configurable in the system. These components of response time may be computed in aggregate or piecewise and corrected for the attributes of a given patient versus the training data from other optimally selected historical patient cohort(s) or the subject patient's own clinical response, for example.

In monitoring delivery and management of care, there may be a plurality of indicators that care providers use in executing their protocols. Typically, there is a primary metric 305 such as body temperature, blood cell counts and chemistry, blood pressure, saturated oxygen, weight, blood sugar, respiration rate, pulse, exhalation air volume, etc. Historically, clinical devices are designed to measure these metrics individually, leaving it up to the care provider to synthesize and the clinical enterprise to acquire hardware devices. Electronic Medical Records and other specialized software receives these data and enable alarms to be set on the metrics which prompt the attention of care providers to respond. Certain examples provide technological improvements to the system 100 beyond enabling alarms and, alternatively or in addition, automatically controls for the response of one or more indicators before or after an intervention as a component of a clinical care delivery orchestration system 100, for example. Beyond the one primary metric 305, a plurality of metrics 315 are managed across time 310, history 317, current value 319, predicted future(s) 320, etc., to directed resource usage, configuration, and clinical activity.

For a plurality of metrics 315, each time series of clinical data 345 is captured at a rate prescribed by the analytical time constant 342 derived by the system to compute clinical response rate 332 and acceleration change 334 for the one or more metrics 305, 315. In certain examples, time constant, $t_c$, 342 is computed to a) lower prediction error in time 320 on paths bounded by limits 325 to 327 and 329 for action(s) 330 and/or b) avoid clinical workflow triggers 339, 340. Time 310 is categorized as having occurred 317, being in real time or near real time 319, and at a future time 320. The time for clinical responses of the plurality of metrics is observed 344 in historical 317 time for a change in metric 345 resulting from an event 331 which may be a) an event that occurs in the unplanned history of the patient, b) a directed intervention, c) a determined time point set for the purposes of computing the change in metrics or rates of change 332 or acceleration of rates of change 334, d) a response time to direct clinical care providers or delivery of therapy, etc.

For patients, each of whom is unique and preferably not experiencing negative clinical states, the system 100 does not a priori have their clinical responses 305, 315 to a directed or non-directed event 331. Further, the response time Rt 344, $Rt_f$ 355 to a medical intervention for clinical workflow and therapy to effect a change is not yet known. A two-step method of estimating the responses (e.g., a computed response time, Rct, 346) is to first compare a current patient with a system-selected composite of historical patients with similar physiological and biological attributes whose responses have already been characterized and infer these to the current patient, and then, second, to inject an event 331 to observe 344 a given patient and healthcare provider response to the event 331. The response rate may include various clinical activity in its computation.

For the plurality of metrics being managed, certain examples enable a higher probability that a clinical intervention before one or more metrics crosses an unacceptable threshold occurs. In an example, one of the metrics 315 being managed is represented by measurements 345 of that metric over a historical time interval 317 up to the current value 325 at time 319. The metric may progress in future time to a state that is clinically unacceptable 340 and, ideally, would not require an unscheduled intervention at point 330. The system forecasts the likely metric value and response time to an intervention on a rolling forward basis. To avoid an unscheduled intervention in future time 320 at point 330, a scheduled intervention must occur before time 330 with sufficient duration that the care provider(s), clinical procedure and medical effects all occur first. These durations are first estimated 346 and then, depending upon the criticality or uncertainty of a specific patient's response, a controlled test event 331 is placed for the purposes of observing this patient's response 344. Regardless of the method used to compute response time, the scheduled intervention must occur such that the forecasted response time, $Rt_f$ 355 prevents the targeted level 340 from occurring.

Certain examples compute probabilistic likely future clinical metric(s) level and staff response time as well as the time needed to deliver care and have medical effects to administered therapy. From the predicted future point at the limit of the undesirable clinical condition state to be avoided, the time required for response is subtracted and clinical workflows are scheduled between the current time 319 and future time 355. If time 355 is exceeded and the clinical condition degrades further 339, 330, then the care quality is impacted. The duration of time for the medical staff to respond, a component 344 of response, is influenced by the workload on staff at points in time. In time spans where multiple patients require care, the response time 346 is longer than it otherwise would have been had no other care been delivered. Certain examples seek to pre-schedule interventions and configure associated resources to avoid such instances.

For example a change in a primary or secondary metric compared to a change in response and a change in the primary or second metric compared to a computed response can be used to adjust milestones or tasks in a care pathway protocol to introduce medical devices, medical instruments, imaging scanners, system-driven treatment protocols and associated apparatus (e.g., spirometry, medication, etc.) before the care pathway diverges to an undesirable state that impacts the health of the patient, device usage, system configuration, workflow, etc.

Figure 4:
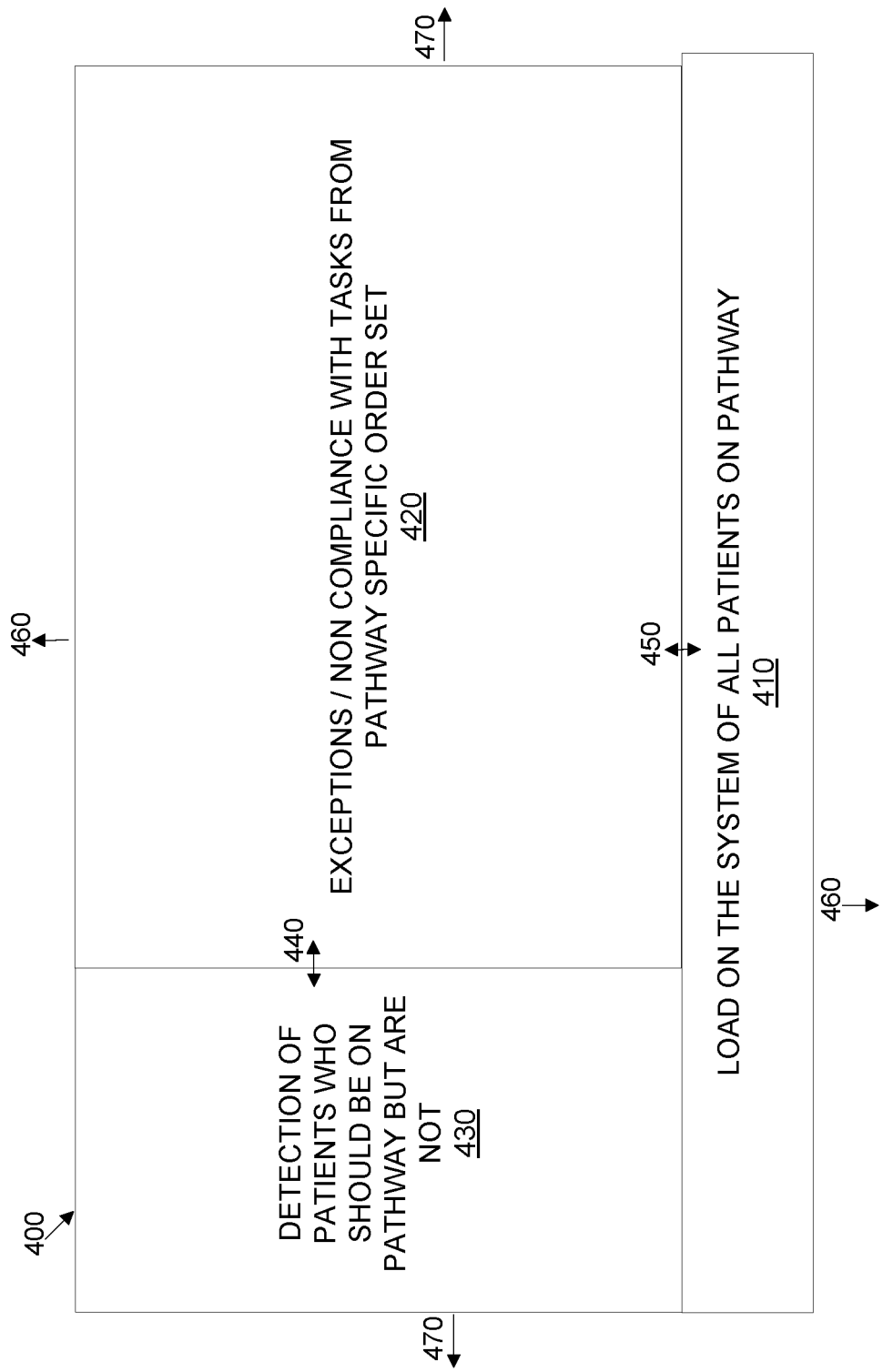
FIG. 4 illustrates an example graphical user interface to organize patients according to care pathway and care pathway compliance.

FIG. 4 illustrates an example graphical user interface 400 driven by the command center engine 102 and including information from departmental systems 104, the workflow and reasoning engine 224, etc., to organize patients according to care pathway and care pathway compliance. The example interface 400 organizes incoming patient, treatment, and care pathway information into three separate areas 410, 420, 430 of the interface display 400. These separate areas 410-430 provide a new graphical user interface 400 capability and a new interaction for users and automated systems managing patient care and care pathway compliance. The allocated space of the graphical user interface is dynamic and a function of the comparative quantity and urgency of the monitored and managed patient population and the care resources serving them, for example.

For example, as shown in FIG. 4, a first area 410 gathers, processes, and displays a total load on the system 100, 200 and its resources for all patients on care pathways associated with the healthcare facility. A user can view and interact with the load information via the interface area 410, including access to equipment (e.g., imaging devices, monitors, information systems, medical devices/instruments, etc.) associated with the care pathways that contribute to the load on the facility, for example.

A second area 420 displays exceptions and/or other non-compliance with tasks from a care pathway-specific order set. A user can view and interact with the exception/non-compliance task information via the interface area 420, including access to details regarding the tasks, warning indicators regarding the tasks, and configuration information for equipment (e.g., imaging devices, monitors, information systems, medical devices/instruments, etc.) associated with the tasks, for example.

A third area 430 displays a list of patients who should be on care pathways but are not being treated according to a care pathway. A user can view and interact with the list of patients via the interface area 430 to view patient records, interact with patient status information and/or time data, interact with warnings and/or summary of patient status, see patient location, etc.

Figure 6:
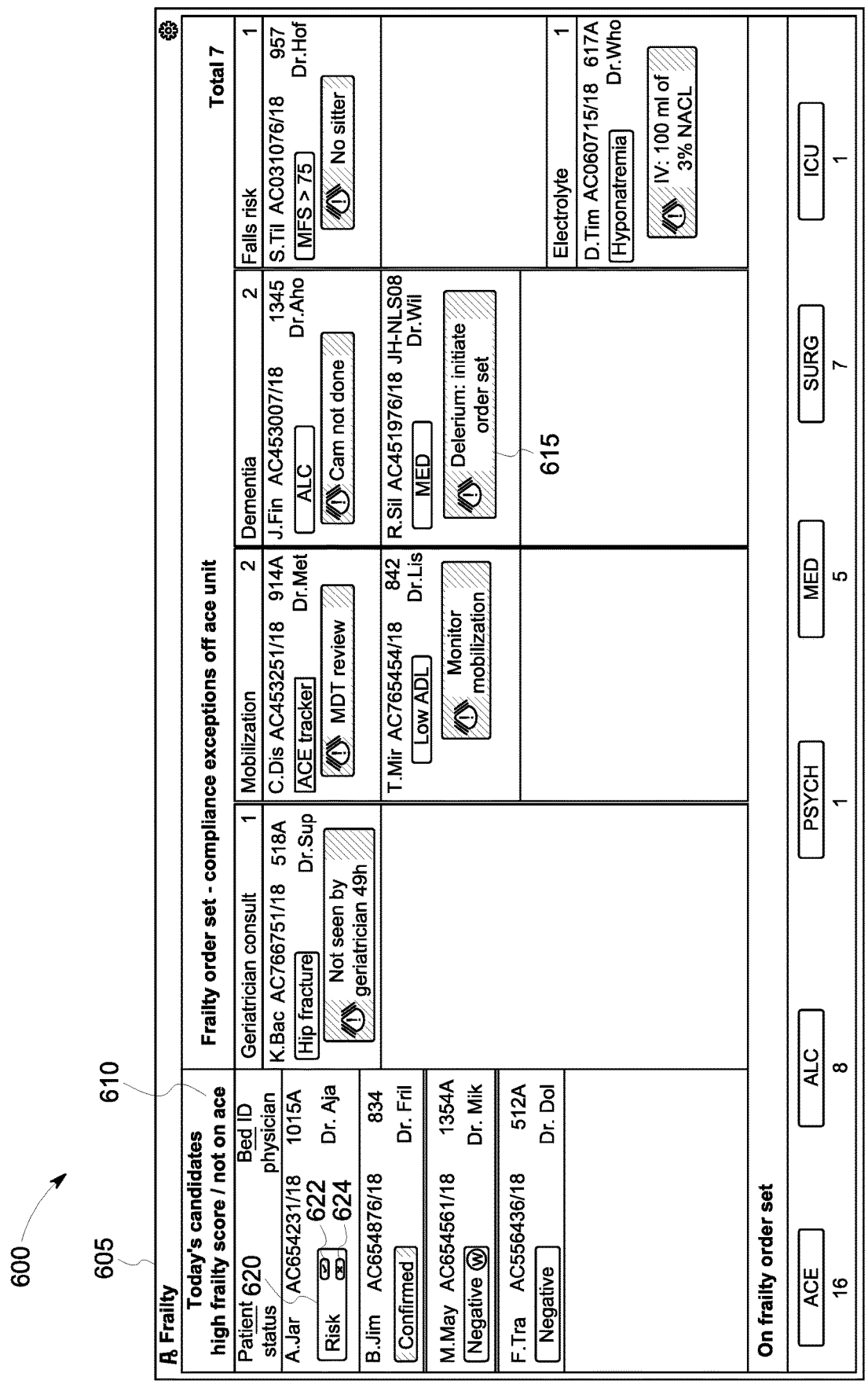

The allocation of screen space to functions 410, 420, 430 is made by the system according to the specified size of the indicated items of FIGS. 5 and 6. The boundaries of display 440, 450 are allocated in a constrained tile 400 area, or, if available, tile 400 area may be increased in the horizontal 470 and/or vertical 460. The location of the tile may be moved in the x-y plane 470, 460 in orientation to other displayed tiles, according to priority or other criteria.

Thus, FIG. 4 provides a classification of patients with respect to care pathways and associate protocols involving various healthcare systems, devices, and/or other resources. Further, it provides a patient view 420, 430 and a 'global view' 410 of relevant patient cohorts and/or care providers tied to those patients. The graphical user interface 400 is a system control that orchestrates care delivery. In the example interface 400, the comparative area 410, 420, 430 size and position, as well as displayed metrics, icons and status, are allocated computationally and adjusted as patient states or care delivery resources change and/or as future prediction requires actions in the current time, for example.

The example interface 400 can detect and categorize patient(s) who should be on a targeted care pathway but are not yet placed there, so that the system 100 and/or a user can act to place them on the care pathway and trigger associated clinical protocols and other tasks to treat the patient. Thus, a user can view patients who are 420 and are not 430 on particular care pathway(s) as well as view the sum of all patients on the care pathway(s) being managed 420 by the healthcare facility. Associated patient clinical state and care providers can be forecast forward in a rolling time horizon via the example interface 400. Staff task frequency and duration per unit time can be aggregated, and the response time 346 for care to a currently monitored patient can be computed. Alternatively or in addition, the care delivery and patient's clinical response can be computed a priori of the degraded clinical condition, and the system provides automated clinical alerts for action now via the interface 400 to avoid an unacceptable 339 clinical condition or staff overload in future time 320, for example.

FIG. 5 depicts an example care pathway management interface 500 showing a managed care pathway driven by the command center engine 102. A sepsis care pathway 505 is described as an illustrative example only. Patients are categorized as being prone to, being diagnosed as, or have been diagnosed as having a targeted clinical condition 510 or having the condition and being actively managed with protocols 515, for example. An example protocol 517 in a sepsis care pathway is prescribing a course of antibiotics as a clinical workflow task being managed by the system. The antibiotics, the care provider and timing of administration(s) are controlled to bring the clinical metric(s) 300 to a desired state in a desired time 319, 320 for a given patient. Types 520 of the clinical condition that is being controlled are computed and displayed.

There are typically a plurality of patients and the combined reaction times are beneficially managed. A workflow load and reaction time on care providers 525 is computed 100 in the current time 319 and predicted at a future time 320. Clinician overload with respect to delivering the protocol tasks for the cohort of patients is determined and alerted or managed. A directed clinical task is provided in alert or prescribed form, optimized for acuity, for example. Certain icons 530 provide visual indicators to care providers for care pathway, protocol, workflow, location, timing and alerts, etc.

FIG. 6 illustrates an example classification of patients into a plurality of care pathway designations with prescribed clinical tasks via a graphical user interface 600. The graphical user interface 600 drives a system control that orchestrates care delivery, for example. The example interface 600 illustrates an example frailty care pathway 605 for purposes of illustration only. The frailty care pathway includes a plurality of protocols being managed across a number of patients. Patients may have, for example, delirium conditions being managed 615 now in response to current clinical metrics or have current interventions and therapy delivered at the current or present time 319 to avoid a future 320 time degradation or staff overload. Patients at risk of developing the targeted conditions 610 are shown for selection to initiate a care pathway and/or provide further monitoring, etc.

As shown in the example of FIG. 6, one or more icons 620 can provide a graphical representation of patient status. In certain examples, the icon 620 can include one or more action buttons, triggers, switches, and/or other selectable items 622, 624 to take an action via the icon 620. For example, as shown in FIG. 6, the icon 620 indicates that the system (e.g., the analytics engine 108, the workflow and reasoning engine 224, etc.) has determined that the associated patient is not on a frailty care pathway but is at risk of negative health outcomes associated with frailty. The example risk icon 620 provides options for the user to confirm 622 that the patient is at risk or override/disagree 624 that the patient is at risk, for example. In certain examples, confirming 622 can place the patient on the frailty care pathway (e.g., with delirium treatment instructions 615, etc.), and denying 624 can remove the patient from being watched via the example interface 600 until additional information regarding the patient is received, the patient condition changes, etc.

In contrast to computers, humans do not process information in a sequential, step-by-step process. Instead, people try to conceptualize a problem and understand its context. While a person can review data in reports, tables, etc., the person is most effective when visually reviewing a problem and trying to find its solution. Typically, however, when a person visually processes information, records the information in alphanumeric form, and then tries to re-conceptualize the information visually, information is lost, and the problem-solving process is made much less efficient over time. The adaptive, compartmentalized interface 400-600 and associated systems 100, 200 help to dynamically update and configure information to automate resource configuration, patient management, and pathway construction and provide a new technological solution to an information organization, viewing, and action problem, particularly in the healthcare systems space.

Thus, certain examples compute, for each patient, multiple potential simulated futures in discrete time steps as well as combinations of clinical workflows, factoring many hypothetical tasks forming a clinical load resulting from all patients. Tens to hundreds of millions of combinations are thus computed 102 to derive the probabilities and optimal assignments and timing being managed. This computing is background to care providers who need summarized, actionable and visual decision criteria that is comprehensible in a moment's time, for example.

Figure 7:
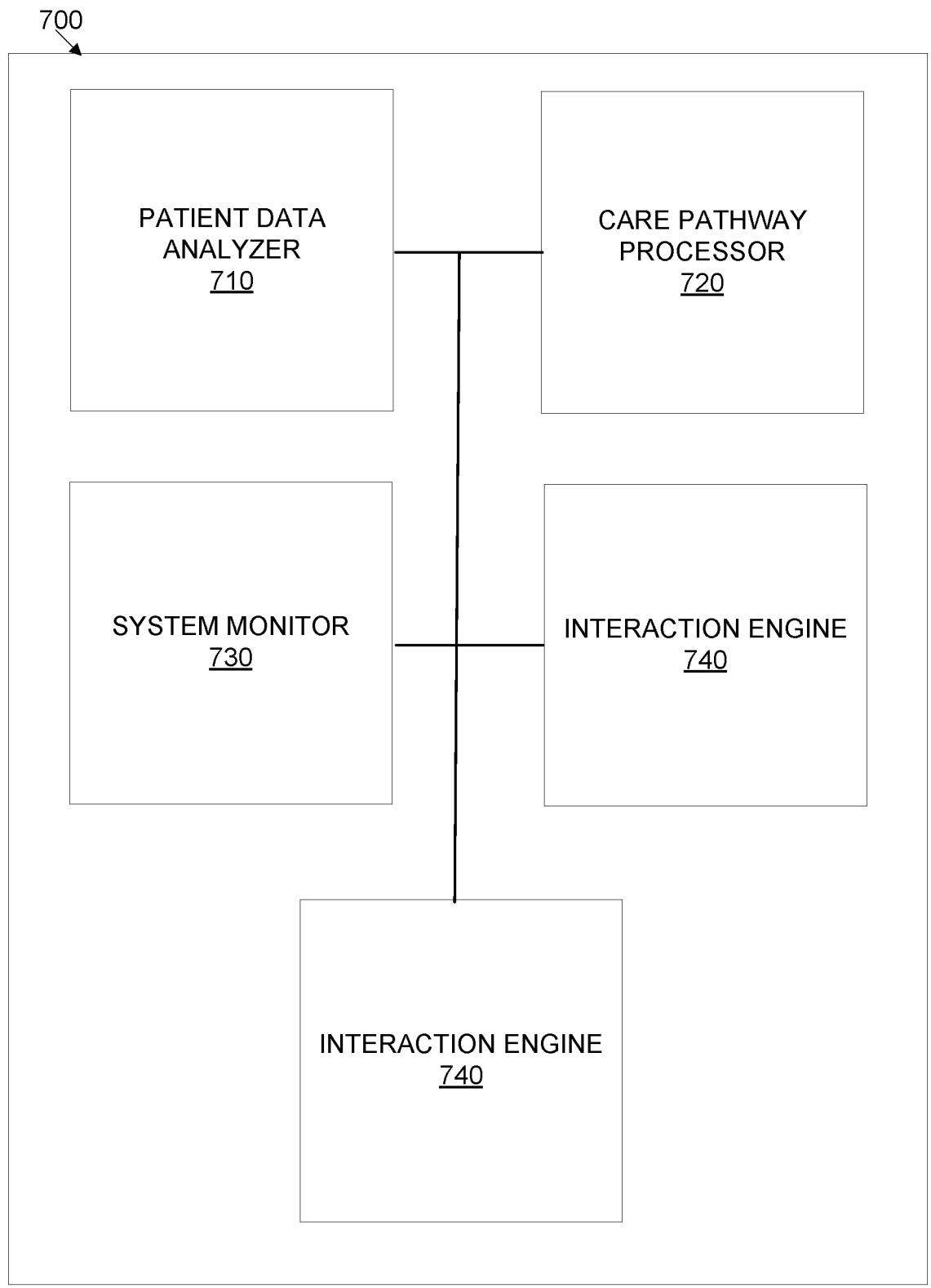
FIG. 7 illustrates an example care pathway management system to enable evolving state protocols and decision support associated with patient care pathways.

FIG. 7 illustrates an example care pathway management system or apparatus 700 to enable evolving state protocols and decision support associated with patient care pathways. The example system 700 can be implemented by one or more of the command center engine 100 (e.g., the analytics engine 108, etc.), the workflow and reasoning engine 224, etc. The example care pathway management system 700 includes a patient data analyzer 710, a care pathway processor 720, a system monitor 730, an interaction engine 740, and a display driver 750. The example patient data analyzer 710 processes available patient data for patients of a healthcare facility to understand the patient population and associate them with application care pathway(s) to which patients are assigned, should be assigned, etc. The care pathway processor 720 models tasks for protocols and/or other actions associated with each available care pathway and can correlate with the patient data analyzer 710 to determine patient status along a care pathway, update a care pathway based on changes to tasks associated with the care pathway, etc. The system monitor 730 monitors a total resource load on the healthcare facility from patients and pathways and draws information from the patient data analyzer 710 and care pathway processor 720 to monitor patient progress along a care pathway, evaluate which patients should be on which pathways, predict likely outcomes for patients on and off particular pathways, etc.

The interaction engine 740 enables one or more users and/or external systems (e.g., an electronic medical record system, a picture archiving and communication system, a radiology desktop, an imaging workstation, an administrative workstation, etc.) to interact with patient and/or care pathway information via the system monitor 730, care pathway processor 720, and patient data analyzer 710. For example, changes can be made to patient records, care pathway prescriptions, associated protocol/task(s), etc., via the interaction engine 740. The display driver 750 can generate a graphical user interface 400-600 to display information on a display screen, etc., and facilitate interaction with the interaction engine 740, for example.

While an example implementation of the apparatus 100, 200, 770 and its interfaces 400-600 are illustrated in FIGS. 1-7, one or more of the elements, processes and/or devices illustrated in FIGS. 1-7 may be combined, divided, re-arranged, omitted, eliminated and/or implemented in any other way. Further, the example command center engine 102, the example workflow and reasoning engine 224, the example care pathway management system 700, etc., may be implemented by hardware, software, firmware and/or any combination of hardware, software and/or firmware. Thus, for example, any of the example command center engine 102, the example workflow and reasoning engine 224, the example care pathway management system 700, etc., can be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example command center engine 102, the example workflow and reasoning engine 224, the example care pathway management system 700, etc., is/are hereby expressly defined to include a non-transitory computer readable storage device or storage disk such as a memory, a digital versatile disk (DVD), a compact disk (CD), a Blu-ray disk, etc. including the software and/or firmware. Further still, the example apparatus 100, 200, 700 and/or their associated interfaces 400-600 of FIGS. 1-7 may include one or more elements, processes and/or devices in addition to, or instead of, those illustrated in FIGS. 1-7, and/or may include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Figure 8:
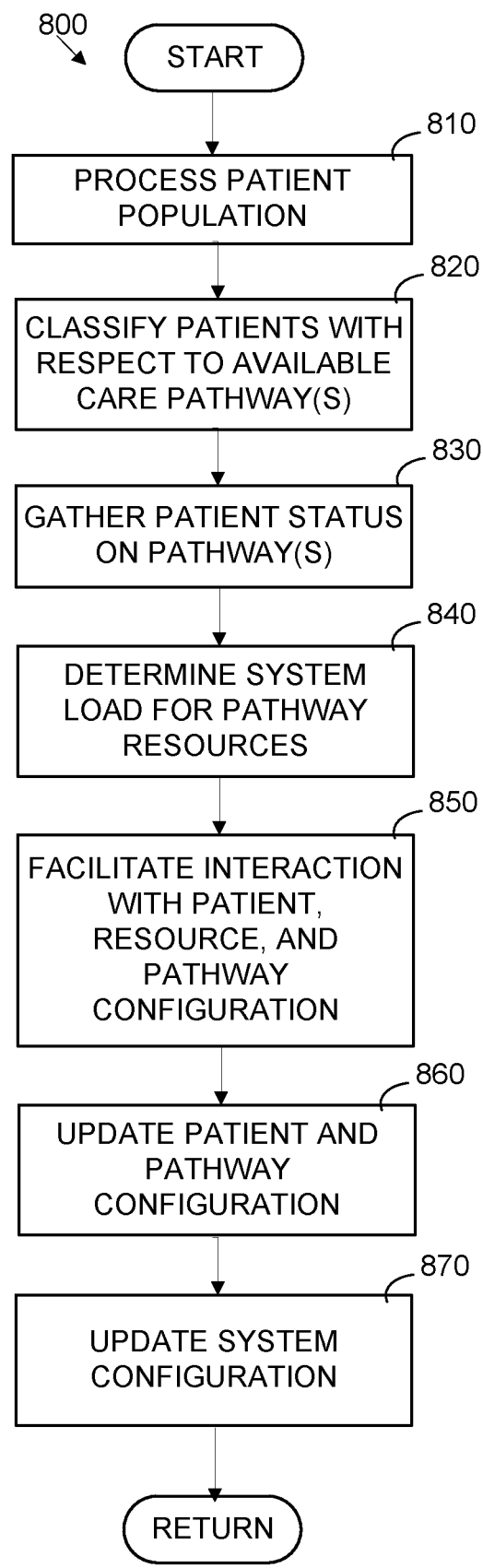
FIGS. 8-9 depict flow diagrams of example methods of classifying patients according to care pathways and monitoring and driving progress along care pathways and associated resource allocation and configuration as shown in the example apparatus and interfaces of FIGS. 1-7.
Figure 9:
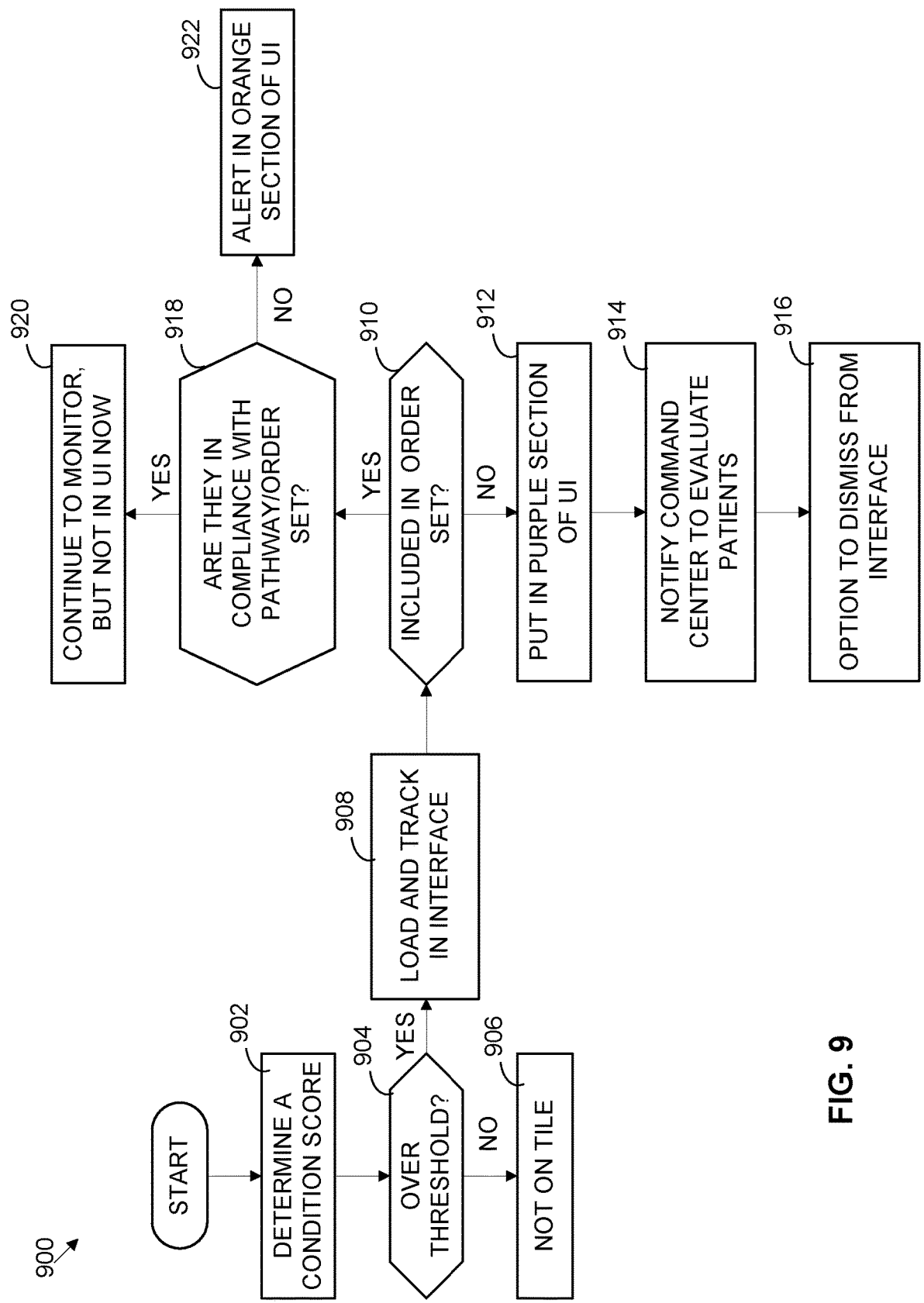

Flowcharts representative of example hardware logic, machine readable instructions, hardware implemented state machines, and/or any combination thereof for implementing the apparatus 100, 200, 700 and their associated interfaces 400-600 of FIGS. 1-7 are shown in FIGS. 8-9. The machine readable instructions may be an executable program or portion of an executable program for execution by a computer processor such as the processor 1012 shown in the example processor platform 1000 discussed below in connection with FIG. 10. The program may be embodied in software stored on a non-transitory computer readable storage medium such as a CD-ROM, a floppy disk, a hard drive, a DVD, a Blu-ray disk, or a memory associated with the processor 1012, but the entire program and/or parts thereof could alternatively be executed by a device other than the processor 1012 and/or embodied in firmware or dedicated hardware. Further, although the example program is described with reference to the flowcharts illustrated in FIGS. 8-9, many other methods of implementing the example apparatus 100, 200, 700 and interfaces 400-600 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

As mentioned above, the example processes of FIGS. 8-9 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, and (3) at least one A and at least one B.

FIG. 8 illustrates a flow diagram of an example method 800 of care pathway management. At block 810, a patient population for a healthcare facility is processed. For example, the example patient data analyzer 710 processes available patient data for patients of a healthcare facility to understand the patient population and associate them with application care pathway(s) to which patients are assigned, should be assigned, etc.

At block 820, patients are classified with respect to available care pathways. For example, the care pathway processor 720 can determine which patients are associated with which pathways, recommend a patient for a care pathway, etc. At block 830, patient status on associated pathway(s) is gathered. For example, the care pathway processor 720 can model tasks for protocols and/or other actions associated with each available care pathway and can correlate with the patient data analyzer 710 to determine patient status along a care pathway.

At block 840, a system load for pathway resources is determined. For example, the system monitor 730 monitors a total resource load on the healthcare facility from patients and pathways and draws information from the patient data analyzer 710 and care pathway processor 720 to monitor resource usage for the healthcare facility according to care pathway, etc.

At block 850, interaction with patient information, resource configuration, and pathway configuration is facilitated. For example, the interaction engine 740 enables one or more users and/or external systems (e.g., an electronic medical record system, a picture archiving and communication system, a radiology desktop, an imaging workstation, an administrative workstation, etc.) to interact with patient and/or care pathway information via the system monitor 730, care pathway processor 720, and patient data analyzer 710. For example, changes can be made to patient records, care pathway prescriptions, associated protocol/task(s), etc., via the interaction engine 740. The display driver 750 can generate a graphical user interface 400-600 to display information on a display screen, etc., and facilitate interaction with the interaction engine 740, for example.

At block 860, patient and pathway configuration is updated. For example, the interaction may assign a patient to a pathway, update a patient's record, adjust a pathway configuration, etc., and the interaction engine 740 works with the system monitor 730, care pathway processor 720, and patient data analyzer 710 to update the respective record, settings, and/or other configuration. At block 870, the system configuration is updated. For example, additional resources may be used and/or may be available based on a care pathway change, a patient reassignment, etc., and the system monitor 730 can update the system configuration and measurement of associated load, for example. Each potential patient's response path through time and, in turn, the associated clinical resource workflow assignment and follow-on interactions of other patients represents a scenario evaluated by the simulation and modeling engines 100, which run continuously in certain example and, in other examples, compute on demand and/or until feasible prediction probabilities and care delivery are planned, through a time horizon.

FIG. 9 illustrates a flow diagram an example method of disposition of patients into care pathway designations and facilitating interaction with patient and care pathway information and configuration. At block 902, a condition score is determined. For example, At block 904, the condition score is evaluated to determine whether the score exceeds and/or otherwise does not satisfy a threshold. For example, a patient's lactate level can be evaluated in comparison to a normal lactate level to determine whether the patient is properly obtaining vasopressor and/or other fluid infusion(s) according to sepsis treatment protocol.

If the condition score does not exceed and/or otherwise satisfies the threshold, then, at block 906, the patient record is not shown on a tile in the graphical user interface 400-600. That is, if the patient's condition score is within normal/expected levels, then the associated condition or exception is likely not concerning, for example. If the score exceeds or does not satisfy the threshold, then, at block 908, the patient record is loaded and tracked on a tile in the interface 400-600 (e.g., in the total load section 410, etc.). That is, if the patient's condition score is outside normal/expected bounds, then the associated condition or exception is likely concerning, for example.

At block 910, the patient record is evaluated to determine if the record is part of an evidence-based order set for a care pathway. If not, then, at block 912, the patient record is added to the portion 430 of the interface including patients who should be on a care pathway but are not. At block 914, adding a patient record to the interface area 430 triggers a notification to the command center engine 102 requesting an evaluation of patients. At block 916, a user and/or automated program can confirm and recommend a patient for a care pathway or dismiss to remove the patient record or indicator from the interface section 430, for example.

If the patient is in the care pathway order set, then at block 918, the patient and associated care pathway order(s) are evaluated with respect to the care pathway definition to determine whether the patient is in compliance with the care pathway and associated protocol/task order set. Such monitoring can be real-time or substantially real-time (including data retrieval, processing, and/or transmission latency, etc.) monitoring of patient care pathway compliance based on system events detected in the healthcare facility and otherwise associated with patient activity and monitored via sensor(s), observed and recorded, and/or otherwise associated with the patient's record.

At block 920, if the patient is non-compliant with the care pathway/order set, then the patient record is added to the exception/non-compliant area 420 of the graphical user interface. An alert can be generated to the patient, family, and/or one or more responsible care providers when a non-compliance and/or other exception is determined, for example.

At block 922, if the patient is in compliance with the care pathway/order set, then the patient and/or the patient's activity continues to be monitored, but the patient's record and/or other indicator is not surfaced for display on the interface 400-600.

Computationally, the system is solving for a per-patient desired state through a planning horizon forward, accounting for diagnostic, delivery, and response. However, actionable tasks and status in the moment may be displayed. The logical elements of dispositioning patient care pathways and planning care delivery for clinical responses computes for the current 319 time and for increments of time 342 over the future 320 time horizon, for example.

Figure 10:
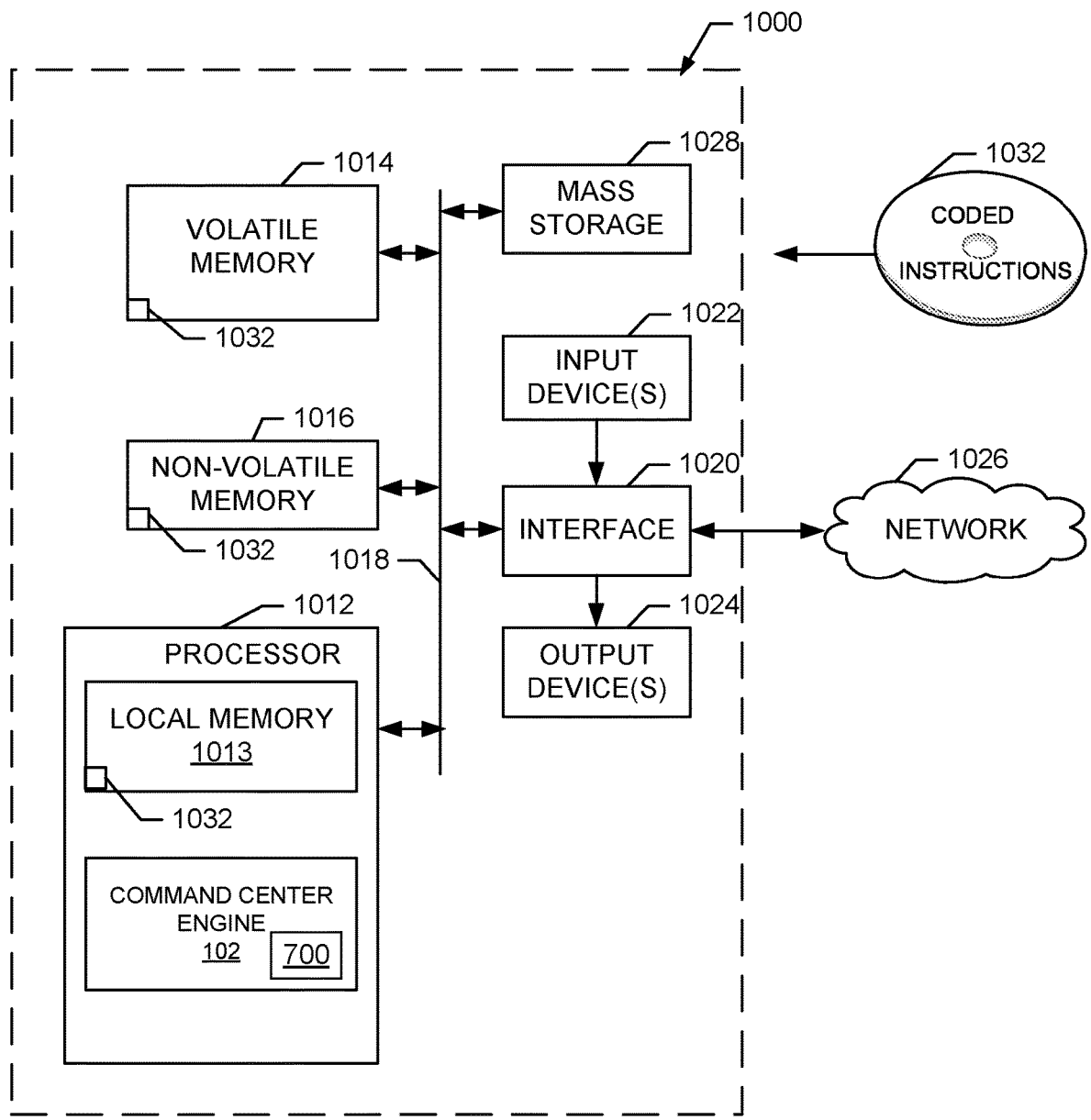
FIG. 10 is a block diagram of an example processing platform structured to execute the instructions of FIGS. 8-9 to implement the apparatus and interfaces of FIGS. 1-7.

FIG. 10 is a block diagram of an example processor platform 1000 structured to execute the instructions of FIGS. 8-9 to implement the apparatus 100, 200, 700, and associated interfaces 400-600 of FIGS. 1-7. The processor platform 1000 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, a headset or other wearable device, or any other type of computing device.

The processor platform 1000 of the illustrated example includes a processor 1012. The processor 1012 of the illustrated example is hardware. For example, the processor 1012 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the example apparatus 100, 224, 700, and its associated interfaces 400-600 can be stored in memory.

The processor 1012 of the illustrated example includes a local memory 1013 (e.g., a cache). The processor 1012 of the illustrated example is in communication with a main memory including a volatile memory 1014 and a non-volatile memory 1016 via a bus 1018. The volatile memory 1014 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1016 may be implemented by flash memory and/or any other desired type of memory device. Access to the main memory 1014, 1016 is controlled by a memory controller.

The processor platform 1000 of the illustrated example also includes an interface circuit 1020. The interface circuit 1020 may be implemented by any type of interface standard, such as an Ethernet interface, a universal serial bus (USB), a Bluetooth® interface, a near field communication (NFC) interface, and/or a PCI express interface.

In the illustrated example, one or more input devices 1022 are connected to the interface circuit 1020. The input device(s) 1022 permit(s) a user to enter data and/or commands into the processor 1012. The input device(s) can be implemented by, for example, an audio sensor, a microphone, a camera (still or video), a keyboard, a button, a mouse, a touchscreen, a trackpad, a trackball, isopoint, goggles, a headset, a motion controller, a sensor, and/or a voice recognition system.

One or more output devices 1024 are also connected to the interface circuit 1020 of the illustrated example. The output devices 1024 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a haptic feedback device, a printer and/or speaker. The interface circuit 1020 of the illustrated example, thus, typically includes a graphics driver card, a graphics driver chip and/or a graphics driver processor.

The interface circuit 1020 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1026. The communication can be via, for example, an Ethernet connection, a digital subscriber line (DSL) connection, a telephone line connection, a coaxial cable system, a satellite system, a line-of-site wireless system, a cellular telephone system, etc.

The processor platform 1000 of the illustrated example also includes one or more mass storage devices 1028 for storing software and/or data. Examples of such mass storage devices 1028 include floppy disk drives, hard drive disks, compact disk drives, Blu-ray disk drives, redundant array of independent disks (RAID) systems, and digital versatile disk (DVD) drives.

The machine executable instructions 1032 of FIGS. 8-9 may be stored in the mass storage device 1028, in the volatile memory 1014, in the non-volatile memory 1016, and/or on a removable non-transitory computer readable storage medium such as a CD or DVD.

From the foregoing, it will be appreciated that example methods, apparatus and articles of manufacture have been disclosed that enable care pathway and associated resource management in a healthcare facility. The disclosed methods, apparatus and articles of manufacture improve the efficiency of using a computing device by providing a particular graphical user interface and particular interaction with patient records, a command center engine, and ordered tasks for protocol and care pathway compliance. The disclosed methods, apparatus and articles of manufacture are accordingly directed to one or more improvement(s) in the functioning of a computer.

Apparatus, systems, and methods are disclosed to automatically manage the tasks of a care pathway and/or associated protocol(s) for one or more patients with technological improvement in at least: (1) a mechanism to automatically manage (re)assignment and (re)configuration of resources in a care delivery enterprise related to a cohort of patients which share care delivery resources whose changing medical condition based upon real time measurements will otherwise overwhelm the care delivery resources; and (2) a mechanism to compute the probability of clinical demand and resource task load through time to optimally schedule interventional clinical actions that will reduce the probabilities of overwhelming care providers and resources in future unscheduled events that would otherwise occur if left to naturally unfold. Certain examples manage complex clinical responses in patients on certain protocols which are influenced by a plurality of care providers, clinical experiences, visitors and the unfolding of time which traverses many shifts and departments. Pathway compliance or exception/non-compliance are determined, and an associated patient record is flagged for certain care for known clinical tasks as well as in the predictive, anticipatory sense to prevent unwanted clinical conditions and subsequent care pathway load. Sensors and systems in the healthcare environment provide input to drive the determination/prediction, and affected systems are reassigned and/or reconfigured when it is determined that a patient is out of compliance or is likely to soon be out of compliance with his/her chosen care pathway. For example, an associated order set and affected systems can be reprogrammed, reserved, triggered, etc., to account for the exception/deviation from the care pathway and/or the underlying clinical metrics which give rise to the changed care pathway, etc.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A care pathway management apparatus comprising:
    a first processor to process patient data for a healthcare facility to compute a clinical response time for patients in a cohort grouping of the healthcare facility;
    a care pathway processor to model tasks for one or more protocols associated with a first care pathway for one or more patients in the cohort grouping and an associated predicted time to execute the modeled tasks, the care pathway processor to prescribe a first task for a resource in a current time for the first care pathway to reduce at least one of a future adverse clinical condition or a future excess response time for one or more patients based on the clinical response time and the predicted time;
a system monitor to coordinate the first processor and the care pathway processor to at least:
identify a first patient record associated with the first care pathway; and
identify a second patient record that is not on the first care pathway but should be on the first care pathway;
a display driver to generate and display a graphical user interface including information regarding the first patient record associated with the first care pathway and the second patient record that should be associated with the first care pathway, the display driver to display the first patient record and associated care pathway information in a first area of the graphical user interface and to display the second patient record in a second area of the graphical user interface, wherein movement of the second patient record to the second area triggers evaluation of the second patient record by the care pathway processor with respect to the first care pathway, wherein the second patient record is associated with the first care pathway based at least on an acceleration of metric change that is computed for one or more metrics in the second patient record; and
wherein the care pathway processor is to facilitate interaction, via the graphical user interface, with the first patient record and the second patient record.

2. The apparatus of claim 1, wherein the care pathway processor is to facilitate interaction with the second patient record to at least one of dismiss the second patient record from the graphical user interface or confirm the second patient record in the second area.

3. The apparatus of claim 2, wherein, when the second patient record is confirmed in the second area, the care pathway processor is to trigger a notification to evaluate the second patient record.

4. The apparatus of claim 1, wherein the display driver is to display a probabilistic system load on resources of the healthcare facility based on patients following care pathways for the healthcare facility in a current instance and a predicted future instance.

5. The apparatus of claim 1, wherein the care pathway processor is to trigger an alert based on feedback from the system monitor when the first patient is not in compliance with at least one of a task order or a clinical state of the first care pathway.

6. The apparatus of claim 5, wherein the system monitor is to trigger an adjustment in at least one of the first patient record or the first care pathway when the system monitor predicts a future undesirable clinical state for the first patient based on evaluation of a clinical metric associated with at least one of the first patient's adherence or response to the first care pathway.

7. The apparatus of claim 6, wherein the adjustment in at least one of the first patient record or the first care pathway triggers a reconfiguration of equipment associated with an order for a set of tasks associated with the first care pathway.

8. A non-transitory computer readable storage medium including instructions which, when executed, cause at least one processor to at least:
process patient data for a healthcare facility to compute a clinical response time for patients in a cohort grouping of the healthcare facility;
prescribe a first task for a resource in a current time for a first care pathway to reduce at least one of a future adverse clinical condition or a future excess response time for one or more patients, the first task selected from a group of modeled tasks for one or more protocols associated with the first care pathway for one or more patients in the cohort grouping and an associated predicted time to execute the modeled tasks;
identify a first patient record associated with the first care pathway;
identify a second patient record that is not on the first care pathway but should be on the first care pathway;
generate and display a graphical user interface including information regarding the first patient record associated with the first care pathway and the second patient record that should be associated with the first care pathway, the graphical user interface to display the first patient and associated care pathway information in a first area of the graphical user interface and to display the second patient record in a second area of the graphical user interface, wherein movement of the second patient record to the second area triggers evaluation of the second patient record by the at least one processor with respect to the first care pathway, wherein the second patient record is associated with the first care pathway based at least on an acceleration of metric change that is computed for one or more metrics in the second patient record; and
facilitate interaction, via the graphical user interface, with the first patient record and the second patient record.

9. The computer readable storage medium of claim 8, wherein the instructions, when executed, cause the at least one processor to facilitate interaction with the second patient record to at least one of dismiss the second patient record from the graphical user interface or confirm the second patient record in the second area.

10. The computer readable storage medium of claim 9, wherein, when the second patient record is confirmed in the second area, the instructions, when executed, cause the at least one processor to trigger a notification to the at least one processor to evaluate the second patient record.

11. The computer readable storage medium of claim 8, wherein the instructions, when executed, cause the at least one processor to display, in a third area of the graphical user interface, a probabilistic system load on resources of the healthcare facility based on patients following care pathways for the healthcare facility in a current instance and a predicted future instance.

12. The computer readable storage medium of claim 8, wherein the instructions, when executed, cause the at least one processor to trigger an alert based on feedback from the system monitor when the first patient is not in compliance with at least one of a task order or a clinical state of the first care pathway.

13. The computer readable storage medium of claim 12, wherein the instructions, when executed, cause the at least one processor to trigger an adjustment in at least one of the first patient record or the first care pathway when the system monitor predicts a future undesirable clinical state for the first patient based on evaluation of a clinical metric associated with at least one of the first patient's adherence or response to the first care pathway.

14. The computer readable storage medium of claim 13, wherein the adjustment in at least one of the first patient record or the first care pathway triggers a reconfiguration of equipment associated with an order for a set of tasks associated with the first care pathway.

15. A computer-implemented method comprising:
processing, by executing an instruction using at least one processor, patient data for a healthcare facility to compute a clinical response time for patients in a cohort grouping of the healthcare facility;

prescribing, by executing an instruction using the at least one processor, a first task for a resource in a current time for a first care pathway to reduce at least one of a future adverse clinical condition or a future excess response time for one or more patients, the first task selected from a group of modeled tasks for one or more protocols associated with the first care pathway for one or more patients in the cohort grouping and an associated predicted time to execute the modeled tasks;

identifying, by executing an instruction using the at least one processor, a first patient record associated with the first care pathway;

identifying, by executing an instruction using the at least one processor, a second patient record that is not on the first care pathway but should be on the first care pathway;

generating and displaying, by executing an instruction using the at least one processor, a graphical user interface including information regarding the first patient record associated with the first care pathway and the second patient record that should be associated with the first care pathway, the graphical user interface to display the first patient and associated care pathway information in a first area of the graphical user interface and to display the second patient record in a second area of the graphical user interface, wherein movement of the second patient record to the second area triggers evaluation of the second patient record by the at least one processor with respect to the first care pathway, wherein the second patient record is associated with the first care pathway based at least on an acceleration of metric change that is computed for one or more metrics in the second patient record; and facilitating interaction, via the graphical user interface by executing an instruction using the at least one processor, with the first patient record and the second patient record.

16. The method of claim 15, wherein facilitating interaction further includes facilitating interaction with the second patient record to at least one of dismiss the second patient record from the graphical user interface or confirm the second patient record in the second area.

17. The method of claim 15, further including displaying, in a third area of the graphical user interface, a probabilistic system load on resources of the healthcare facility based on patients following care pathways for the healthcare facility in a current instance and a predicted future instance.

18. The method of claim 17, further including triggering an adjustment in at least one of the first patient record or the first care pathway when the system monitor predicts a future undesirable clinical state for the first patient based on evaluation of a clinical metric associated with at least one of the first patient's adherence or response to the first care pathway.

19. The method of claim 18, wherein the adjustment in at least one of the first patient record or the first care pathway triggers a reconfiguration of equipment associated with an order for a set of tasks associated with the first care pathway.

20. The method of claim 15, further including adjusting a graphical orientation of icons on the graphical user interface for the first care pathway according to a comparative importance of values associated with the icons at a current time and over a future time horizon.

* * * * *